(12) United States Patent
Focassio et al.

(10) Patent No.: US 10,285,924 B2
(45) Date of Patent: May 14, 2019

(54) DENTAL FLOSS COATING COMPOSITION

(71) Applicant: Colgate-Palmolive Company, New York, NY (US)

(72) Inventors: Paulo Focassio, Sao Paulo (BR); Luma Garcia Lopes de Freitas, Sao Paulo (BR); Marcella Mourao, Sao Paulo (BR)

(73) Assignee: Colgate-Palmolive Company, New York, NY (US)

( * ) Notice: Subject to any disclaimer, the term of this patent is extended or adjusted under 35 U.S.C. 154(b) by 14 days.

(21) Appl. No.: 15/528,621

(22) PCT Filed: Dec. 10, 2014

(86) PCT No.: PCT/US2014/069490
§ 371 (c)(1),
(2) Date: May 22, 2017

(87) PCT Pub. No.: WO2016/093815
PCT Pub. Date: Jun. 16, 2016

(65) Prior Publication Data
US 2017/0252285 A1  Sep. 7, 2017

(51) Int. Cl.
| | | |
|---|---|---|
| A61K 8/22 | (2006.01) | |
| A61K 8/86 | (2006.01) | |
| A61Q 11/00 | (2006.01) | |
| A61C 15/04 | (2006.01) | |
| A61K 8/81 | (2006.01) | |
| B05D 1/18 | (2006.01) | |
| B05D 3/00 | (2006.01) | |
| B05D 7/20 | (2006.01) | |

(52) U.S. Cl.
CPC .............. *A61K 8/86* (2013.01); *A61C 15/041* (2013.01); *A61K 8/22* (2013.01); *A61K 8/8176* (2013.01); *A61Q 11/00* (2013.01); *B05D 1/18* (2013.01); *B05D 3/007* (2013.01); *B05D 7/20* (2013.01); *A61K 2800/31* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 2,772,205 A | 11/1956 | King | |
| 3,830,246 A | 8/1974 | Gillings | |
| 4,638,823 A | 1/1987 | Newman et al. | |
| 5,033,488 A | 7/1991 | Curtis et al. | |
| 5,423,337 A | 6/1995 | Ahlert et al. | |
| 5,503,842 A | 4/1996 | Fazan et al. | |
| 5,603,921 A | 2/1997 | Bowen | |
| 5,680,876 A * | 10/1997 | Hasham | A61C 15/041 132/321 |
| 5,830,495 A | 11/1998 | Ochs | |
| 5,967,155 A | 10/1999 | Marcon | |
| 6,102,050 A | 8/2000 | Marcon | |
| 6,123,982 A | 9/2000 | Fontana | |
| 6,221,341 B1 * | 4/2001 | Montgomery | A61K 8/22 424/49 |
| 6,289,904 B1 | 9/2001 | Suhonen et al. | |
| 6,619,299 B2 | 9/2003 | Marcon et al. | |
| 2002/0074012 A1 | 6/2002 | Marcon et al. | |
| 2003/0230319 A1 | 12/2003 | Marcon et al. | |
| 2006/0024246 A1 * | 2/2006 | Maitra | A61K 8/0208 424/49 |
| 2006/0225765 A1 | 10/2006 | Moore | |
| 2011/0044916 A1 | 2/2011 | Kohli et al. | |

FOREIGN PATENT DOCUMENTS

| | | |
|---|---|---|
| EP | 0637446 B1 | 2/1995 |
| GB | 1451237 | 9/1976 |
| WO | WO 1991/007184 | 5/1991 |
| WO | WO 1994/026245 | 11/1994 |
| WO | WO 1995/030404 | 11/1995 |
| WO | WO 1998/057617 | 12/1998 |
| WO | WO 1999/034772 | 7/1999 |
| WO | WO 1999/062470 | 12/1999 |
| WO | WO 2000/033802 | 6/2000 |
| WO | WO 2009/100276 | 8/2009 |

OTHER PUBLICATIONS

International Search Report and Written Opinion in International Application No. PCT/US2014/069490, dated Jun. 24, 2015.

* cited by examiner

*Primary Examiner* — Nannette Holloman

(57) ABSTRACT

Provided herein is a dental floss coating composition comprising one or more polyethylene glycol polymers and a peroxide source, wherein the melting temperature of the one or more polyethylene glycol polymers, in combination, is from 38 C to 50 C, and wherein the one or more polyethylene glycol polymers are present in the composition in an amount of from 80 weight % to 97 weight % by total weight of the composition. The composition may be used in molten form to coat dental floss while maintaining the stability of the peroxide source.

22 Claims, No Drawings

DENTAL FLOSS COATING COMPOSITION

BACKGROUND

The use of dental floss and other interdental cleaners is an important part of dental hygiene. Dental floss is used to remove plaque and other particulate matter from between the teeth and wider the gum line. These are areas in the mouth where a toothbrush typically cannot reach, and if not cleaned regularly, tooth decay and gum disease may result.

Dental floss typically comprises a mineral, animal or vegetable wax coating, which provides lubricity, and facilitates movement of the floss between teeth. Wax may also prevent the floss fibers from fraying or breaking while it is in use.

It is desirable to incorporate additives such as peroxides, flavorants, sweeteners, and anti-plaque agents into dental floss coatings to impart further therapeutic or cosmetic benefit, or to improve taste.

During manufacturing of the floss, the wax coating is typically melted, additives as described above are optionally incorporated into the molten coating, and the floss is immersed in a bath containing the molten coating. However, mineral, animal and vegetable waxes typically have melting points over 75°. At such high temperatures, some additives become unstable and lose their functionality. In particular, at such high temperatures, peroxide decomposes to oxygen and water and loses its whitening and antimicrobial activity.

It would therefore be desirable to provide a dental floss coating composition which maintains the functions of conventional wax, yet which can be applied to dental floss without negatively impacting on the stability of additives such as peroxide that are incorporated into the coating.

SUMMARY OF INVENTION

The present inventors have found that polyethylene glycol polymers may serve as suitable replacements for wax as dental floss coating materials. In particular, by using one or more polyethylene glycol polymers which, in combination, have a melting point below 50° C., as a dental floss coating composition, it is not necessary to use high heating temperatures to melt the composition during the floss manufacturing process. As such, additives such as peroxide ma be incorporated into the coating composition without significant decomposition that would otherwise be observed at high heating temperatures.

Accordingly, in a first aspect, the present invention provides a dental floss coating composition comprising one or more polyethylene glycol polymers and a peroxide source, wherein the melting temperature of the one or more polyethylene glycol polymers, in combination, is from 38° C. to 50° C., and wherein the one or more polyethylene glycol polymers is present in the composition in an amount of from 80 weight % to 97 weight % by total weight of the composition.

Preferably, the one or more polyethylene glycol polymers have an average molecular weight of from 950 to 9000 Daltons, or from 1000 to 3000 Daltons. More preferably, the one or more polyethylene glycol polymers have an average molecular weight of from 1200 to 1600 Daltons. Most preferably, the one or more polyethylene glycol polymers have an average molecular weight of 1500 Daltons. In other embodiments, the one or more polyethylene glycol polymers have an average molecular weight of from 5000 to 9000 Daltons, or from 6000 to 8000 Daltons.

Optionally, the peroxide source is selected from hydrogen peroxide, peroxides of alkali and alkaline earth metals, organic peroxy compounds, peroxy acids, pharmaceutically acceptable salts thereof and mixtures thereof. Preferably, the peroxide source is hydrogen peroxide. Optionally, the peroxide source comprises a cross-linked polymer and a peroxide compound as provided above. Preferably, the peroxide source comprises cross-linked polyvinylpyrrolidone (PVP)-hydrogen peroxide.

Optionally, the peroxide source is present in the composition in an amount of from 10 weight % to 20 weight %, by total weight of the composition. Further optionally, the peroxide source is present in the composition in an amount of from 10 weight % to 15 weight %, by total weight of the composition. Still further optionally, the peroxide source is present in the composition in an amount sufficient to deliver hydrogen peroxide in an amount of from 1 weight % to 5 weight %, or from 1 weight % to 3 weight %, by total weight of the composition.

Optionally, the composition is substantially anhydrous.

Optionally, the composition further comprises one or more ingredients selected from desensitizing agents, antimicrobial agents, tartar control agents, mouth feel agents, sweeteners, flavorants, colorants, fluoride sources and combinations thereof.

Preferably, the melting temperature of the one or more polyethylene glycol polymers, in combination, is from 42° C. to 48° C. More preferably, the melting temperature of the one or more polyethylene glycol polymers, in combination, is 45° C.

Optionally, the composition comprises polyvinylpyrrolidone (PVP). Further optionally, the composition comprises PVP in an amount of from 1 weight % to 4 weight % by total weight of the composition.

Optionally, the composition comprises a solvent selected from ethanol, isopropylalcohol, and cyclomethicone. Further optionally, the composition comprises the solvent in an amount of from 5 weight % to 15 weight %, by total weight of the composition.

Optionally, the composition is in molten or liquid form.

In a second aspect, there is provided a dental floss comprising a coating composition, wherein the coating composition comprises one or more polyethylene glycol polymers and a peroxide source, wherein the melting temperature of the one or more polyethylene glycol polymers, in combination, is from 38° C. to 50° C., and wherein the one or more polyethylene glycol polymers is present in the composition in an amount of from 80 weight % to 97 weight % by total weight of the composition.

Optionally, the coating composition is defined as herein.

Optionally, the dental floss comprises at least one segment which is not coated with the coating composition. Preferably, the dental floss comprises a plurality of segments which are not coated with the coating composition.

Optionally, the dental floss is comprised of one or more of polyamide, polyethylene, PTFE (polytetrafluoroethylene), polypropylene, and polyurethane.

In a third aspect, the present invention provides a method of coating dental floss, wherein the method comprises:

a) heating a coating composition to a temperature no greater than 50° C. to form a molten composition, wherein the composition comprises one or more polyethylene glycol polymers and a peroxide source, wherein the melting temperature of the one or more polyethylene glycol polymers, in combination, is from 38° C. to 50° C., and wherein the one or more polyethylene glycol polymers is present in the composition in an amount of from 80 weight % to 97 weight % by total weight of the composition, b) applying the molten composition to dental floss to coat the floss, and c) cooling the composition so as to solidity the composition on the dental floss.

Optionally, the composition is heated to a temperature of from 38° C. to 50° C. Further optionally, the composition is as defined herein.

In a fourth aspect, there is provided a dental floss obtained by the method defined herein.

In a fifth aspect, there is provided a use of one or more polyethylene glycol polymers, in a dental floss coating composition comprising a peroxide source, to prevent or reduce decomposition of the peroxide source in the composition in molten form, wherein the melting temperature of the one or more polyethylene glycol polymers, in combination, is from 38° C. to 50° C., and wherein the one or more polyethylene glycol polymers is present in the composition in an amount of from 80 weight % to 97 weight % by total weight of the composition.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Unless otherwise specified, all polymer molecular weights are calculated by weight average.

In one arrangement, provided herein is a dental floss coating composition comprising one or more polyethylene glycol polymers and a peroxide source, wherein the melting temperature of the one or more polyethylene glycol polymers, in combination, is from 38° C. to 50° C., and wherein the one or more polyethylene glycol polymers is present in the composition in an amount of from 80 weight % to 97 weight % by total weight of the composition.

The term "dental floss" shall be herein understood to include both dental floss and dental tape, as well as any other similar article. Moreover, the dental floss referred to herein may include any suitable or commercially available dental floss or tape.

Polyethylene Glycol

Polyethylene glycol refers to an oligomer or polymer of ethylene oxide. The present inventors have found that polyethylene glycol effectively enhances the lubricity of floss and prevents fraying or breaking of floss fibers. Thus, polyethylene glycol is a suitable base for dental floss coating and may be used in place of conventional waxes.

By "base" it is meant that polyethylene glycol is the most abundant component of the coating composition (by weight). In some embodiments, the coating composition comprises polyethylene glycol in an amount of from 78 weight % to 95 weight %, from 78 weight % to 90 weight %, from 78 weight % to 85 weight %, or from 78 weight % to 83 weight %, by total weight of the composition. In some embodiments, the coating composition comprises polyethylene glycol in an amount of from 80 weight % to 95 weight %, from 80 weight %, to 90 weight %, from 80 weight % to 85 weight %, or from 80 weight % to 83 weight %, by total weight of the composition. In other embodiments, the coating composition comprises polyethylene glycol in an amount of from 85 weight % to 97 weight %, from 85 weight % to 95 weight %, from 85 weight % to 90 weight %, or from 85 weight %, to 87 weight % by total weight of the composition. Preferably, the coating composition comprises polyethylene glycol in an amount of from 80 weight % to 90 weight %, or from 80 weight % to 87 weight %, by total weight of the composition.

In some embodiments, the coating composition comprises only one type of polyethylene glycol polymer having a melting point of from 38° C. to 50° C. In other embodiments, the coating composition comprises a mixture of polyethylene glycol polymers. In these embodiments, the melting point of the polymers, in combination, is from 38° C. to 50° C. The melting point of the polymers "in combination" refers to the melting point of the solid formed by combining each of the polymers in the desired proportions to form a liquid mixture, and allowing the mixture to cool so as to form the solid.

In some embodiments, the melting point of the one or more polyethylene glycol polymers, in combination, is from 40° C. to 50° C., or from 45° C. to 50° C. In other embodiments, the melting point of the one or more polyethylene glycol polymers, in combination, is from 40° C. to 48° C., from 40° C. to 45° C., from 42° C. to 48° C. or from 42° C. to 45° C. In a preferred embodiment, the melting point of the one or more polyethylene glycol polymers, in combination, is 45° C. It is undesirable to incorporate one or more polyethylene glycol polymers, which, in combination, have a melting point below 38° C. This is to ensure that the coating does not melt in the hands of the user when applying the dental floss. If the melting temperature is above 50° C., then during manufacture of the floss, it would be necessary to heat the composition to above 50° C. in order to form a molten composition which can be used to coat the floss. At temperatures above 50° C., peroxide becomes unstable and decomposes to oxygen and water. In some embodiments, the composition is provided in molten or liquid form.

Polyethylene glycols are prepared by polymerization of ethylene oxide and are commercially available over a wide range of molecular weights from 300 Da to 10,000,000 Da. The higher the molecular weight, the greater the number of monomeric units in the polymer molecule, and the greater the melting point. All polymer weights provided herein are based on weight average. In some embodiments, the one or more polyethylene glycol polymers have an average molecular weight of from 950 to 9000 Da, or from 1000 to 8000 Da, or from 2000 to 6000 Da, or from 3000 to 5000 Da. In other embodiments, the one or more polyethylene glycol polymers have an average molecular weight of from 1000 to 9000 Daltons, or from 1000 to 8000 Da, or from 1000 to 7000 Da, or from 1000 to 6000 Da, or from 1000 to 5000 Da, or from 1000 to 4000 Da, or from 1000 to 3000 Da, or from 1000 to 2000 Da. In further embodiments, the one or more polyethylene glycol polymers have an average molecular weight of from 1000 to 1800 Daltons, or from 1000 to 1700 Da, or from 1000 to 1600 Da, or from 1000 to 1500 Da, or from 1000 to 1400 Da, or from 1000 to 1300 Da, or from 1000 to 1200 Da. In preferred embodiments, the one or more polyethylene glycol polymers have an average molecular weight of from 1200 to 1600 Da, and more preferably, 1500 Da. When more than one polyethylene glycol monomer is present, the "average molecular weight" refers to the weighted average molecular weight of the polymers, thus taking into account the relative concentrations of each polymer.

Polyethylene glycols having high average molecular weights (for example, from 5000 to 9000 Da) are often preferred in the coating compositions defined herein, since they have less solubility in water as compared to polyethylene glycols having low average molecular weights. Consequently, compositions comprising the high molecular weight polymers and a peroxide source have less peroxide-associated irritating effects when brought into contact with the skin of the user. (The floss coating compositions comprising high molecular weight polyethylene glycol polymers nevertheless have sufficient solubility to release the peroxide source in the interdental space during use of the floss.) Accordingly, in some embodiments, the one or more polyethylene glycol polymers have an average molecular weight of from 5000 to 9000 Da, or from 6000 to 9000 Da, or from 7000 to 9000 Da, or from 8000 to 9000 Da. In other embodiments, the one or more polyethylene glycol polymers have an average molecular weight of from 5000 to 8000 Da, or from 6000 to 8000 Da, or from 7000 to 8000 Da. In further embodiments, the one or more polyethylene glycol polymers have an average molecular weight of from 5000 to 7000 Da, or from 6000 to 7000 Da.

However, molten compositions comprising polyethylene glycol polymers having a high average molecular weight may have an undesirably high viscosity which causes difficulties during the floss coating process. For example, viscous compositions may result in an uneven or an inconsistent coating of the floss. Furthermore, in viscous compositions, peroxide sources such as cross-linked PVP-hydrogen peroxide and other additives such as PVP may fall out of suspension. The viscosity of such coating compositions may be reduced by incorporating a volatile solvent into the coating composition. Suitable volatile solvents include without limitation, ethanol, isopropyl alcohol and cyclomethicone. Such solvents may be incorporated into the coating composition in an amount of from 5 weight % to 15 weight %, or from 5 weight % to 10 weight %, or from 5 weight % to 8 weight %, by total weight of the composition. In some arrangements, the volatile solvent is incorporated into the coating composition in an amount of from 7 weight % to 15 weight %, or from 7 weight % to 10 weight %, by total weight of the composition. In further arrangements, the volatile solvent is incorporated into the coating composition in an amount of from 10 weight % to 15 weight %, by total weight of the composition. The concentration of the volatile solvent may be adjusted depending on the average molecular weight of the polyethylene glycol polymers in the composition.

Preferably, to achieve optimal coating with the peroxide source, the viscosity of the coating compositions is from 1 cm$^2$/second to 3 cm$^2$/second, as measured at 25° C. using Brookfield Model LVTDV-II with Spindle 1. The volatile solvent may be incorporated into the coating composition in an amount sufficient to achieve such as viscosity.

In a preferred embodiment, the coating composition comprises one or more polyethylene glycol polymers have an average molecular weight of from 5000 to 9000 Da, or from 5000 to 8000 Da, or from 5000 to 7000 Da, or from 5000 to 6000 Da, and a volatile solvent selected from ethanol, isopropyl alcohol, and cyclomethicone. The solvent may be present in the amounts defined above.

During the floss manufacturing/coating process (see below) and specifically at low temperatures of from 38° C. to 50° C. which are used in the floss coating processes defined herein, the solvents typically evaporate from the coating composition.

Peroxide Source

The coating compositions provided herein comprise a peroxide source. The term "peroxide source" refers to any orally acceptable peroxide compound (i.e. an oxidizing compound that comprises a bivalent oxygen-oxygen group). The peroxide source is preferably miscible with the polyethylene glycol.

Exemplary peroxide compounds include hydroperoxides hydrogen peroxide, organic peroxy compounds, peroxy acids, pharmaceutically-acceptable salts thereof, and mixtures thereof. Organic peroxy compounds include urea peroxide, glyceryl hydrogen peroxide, alkyl hydrogen peroxides, dialkyl peroxides, alkyl peroxy acids, peroxy esters, diacyl peroxides, benzoyl peroxide, and mixtures thereof. Peroxy acids and their salts include organic peroxy acids such as alkyl peroxy acids and mixtures thereof, as well as inorganic peroxy acid salts such is and perborate salts of alkali and alkaline earth metals (e.g. lithium, potassium, sodium, magnesium, calcium and barium), and mixtures thereof. Preferred solid peroxides are sodium perborate, sodium percarbonate, urea peroxide, and mixtures thereof. In some embodiments, the peroxide compound may be bound to a polymer such as PVP (poly-N-vinylpyrrolidone). Suitable PVP complexes would be known to a person skilled in the art of oral care, and are also disclosed, for example, in U.S. Pat. No. 5,122,370, the contents of which are incorporated herein by reference in their entirety. Linear PVP peroxide and cross-linked PVP peroxide sold as Peroxydone™ from ISP Corp. are also peroxide compounds useful as whitening agents in the present invention. PVP-hydrogen peroxide can be effectively produced by mixing linear PVP or cross-linked PVP with concentrated liquid hydrogen peroxide in the dentifrice.

Typically, the peroxide source comprises a peroxide compound selected from: urea peroxide, sodium percarbonate, sodium perborate, cross-linked PVP-hydrogen peroxide complex, and mixtures thereof. In a preferred embodiment, the peroxide source comprises cross-linked PVP-hydrogen peroxide. Cross-linked PVP-hydrogen peroxide has enhanced stability.

Typically, the peroxide source is present in the coating composition in an amount of from 0.1 weight % to 40 weight %, or from 1 weight % to 30 weight %, or from 5 weight % to 20 weight % by total weight of the composition. Preferably, the peroxide source is present in the composition in an amount of from 10 weight % to 20 weight %, or from 10 weight % to 15 weight %, or from 8 weight % to 20 weight %, or from 8 weight % to 15 weight %, by total weight of the composition. In some embodiments, the peroxide source is present in the composition in an amount of from 10 weight % to 15 weight %, or from 11 weight % to 15 weight % by total weight of the composition, or from 12 weight % to 15 weight %, or from 13 weight % to 15 weight %, by total weight of the composition. Preferably, the peroxide source is present in the composition in an amount of from 10 weight % to 13 weight %, or from 10 weight % to 14 weight % by total weight of the composition. Typically, the peroxide source is present in the composition in an amount of 13 weight % by total weight of the composition. In the embodiments provided above, optionally, the peroxide source is cross-linked PVP-hydrogen peroxide.

Preferably, the peroxide source is present in the composition in an amount sufficient to deliver hydrogen peroxide in an amount of from 0.1 weight % to 5 weight %, or from 0.5 weight % to 5 weight %, or from 1 weight % to 5 weight %, or from 2 weight % to 5 weight %, or from 3 weight % to 5 weight % by total weight of the composition. In some embodiments, the peroxide source is present in the composition in an amount sufficient to deliver hydrogen peroxide in an amount of from 0.25 weight % to 3 weight %, or from 0.5 weight % to 3 weight %, or from 1 weight % to 3 weight %, or from 2 weight % to 3 weight %, by total weight of the composition. In further embodiments, the peroxide source is present in the composition in an amount sufficient to deliver hydrogen peroxide in an amount of from 0.5 weight % to 2 weight %, or from 1 weight % to 2 weight %, by total weight of the composition.

Other Ingredients

The coating compositions defined herein may comprises one or more further ingredients selected from desensitizing agents, antimicrobial agents, tartar control agents, mouth feel agents, sweeteners, flavorants, colorants, fluoride sources and combinations thereof. Examples of such ingredients would be known to a person skilled in the art of oral care. However, some non-limiting examples are provided below.

Flavorants

The coating compositions provided herein may include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

Fluoride Ion Source

The coating compositions may further comprise a fluoride ion source. Fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof.

Desensitizing Agents

The compositions provided herein optionally incorporate one or more desensitizing agents. These include, without limitation, potassium salts such as potassium nitrate, potassium bicarbonate, potassium chloride, potassium citrate, and potassium oxalate; capsaicin; eugenol, strontium salts; zinc salts; chloride salts and combinations thereof.

Mouth-Feel Agents

Mouth-feel agents that may be incorporated into the compositions defined herein include materials which impart a desirable texture or other feeling during use of the floss. Such agents include bicarbonate salts, which may impart a "clean feel" to teeth. Any orally acceptable bicarbonate can be used, including, without limitation, alkali metal bicarbonates such as sodium and potassium bicarbonates, ammonium bicarbonate, and mixtures thereof.

Sweeteners

The compositions provided herein may optionally comprise a sweetener. Sweeteners which may be used in the compositions of the present invention include artificial sweeteners such as saccharin, acesulfam, neotam, cyclamate or sucralose; natural high-intensity sweeteners such as thaumatin, stevioside or glycyrrhizin; or sugar alcohols such as sorbitol, xylitol, maltitol or mannitol.

Colorants

The compositions provided herein may comprise at least one colorant. Colorants herein include pigments, dyes and agents imparting a particular luster or reflectivity such as pearling agents. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like.

Antimicrobial Agents

Preservatives, such as chlorhexidine, triclosan, quaternary ammonium compounds (such as benzalkonium chloride) or parabens (such as methyl or propyl paraben) may be incorporated in the compositions provided herein.

Thickening Agents

Thickening agents which may be incorporated into the compositions defined herein include natural and synthetic gums and colloids. Suitable thickening agents include naturally occurring polymers such as carrageenan xanthan gum poly glycols of varying molecular weights sold under the tradename Polyox, and polyvinylpyrrolidone (PVP). Compatible inorganic thickening agents include amorphous silica compounds and colloidal silica compounds available under the trade designation Zeodent manufactured by Huber Corporation. Other inorganic thickening agents include natural and synthetic clays such as hectorite clays lithium magnesium silicate (laponite) and magnesium aluminum silicate (Veegum). PVP is a particularly preferred thickener since PVP retards the degradation of peroxide compounds such as PVP-peroxide. Additionally, coating compositions comprising PVP are more stable with less tendency for sedimentation. PVP may be present in the coating composition in an amount of from 1 to 5 weight %, from 1 weight % to 4 weight %, from 1 to 3 weight %, or from 1 weight % to 2 weight %, by total weight of the composition. Optionally, PVP is present in the coating composition in an amount of from 2 weight % to 4 weight, or from 2 weight % to 3 weight %, by total weight of the composition. In some embodiments, the PVP is present in the coating composition in an amount of 2 weight %, by total weight of the composition.

The coating compositions described herein are typically substantially anhydrous. By "substantially" anhydrous it is meant that the compositions comprise less than 3%, less than 2%, less than 1%, less than 0.5%, less than 0.3%, less than 0.2%, or less than 0.1% water by total weight of the composition. Peroxide is unstable in aqueous conditions, and thus by employing an anhydrous composition, peroxide decomposition is minimized.

Furthermore, the coating compositions described herein are typically free of ingredients that have melting points below 38° C. or above 50° C. For example, in some embodiments, the coating compositions are free of animal, vegetable and/or synthetic waxes.

Methods and Uses

The coating compositions defined herein are suitable for coating dental floss. Accordingly, in one arrangement, there is provided a dental floss comprising a coating composition, wherein the coating composition comprises one or more polyethylene glycol polymers and a peroxide source, wherein the melting temperature of the one or more polyethylene glycol polymers, in combination, is from 38° C. to 50° C., and wherein the one or more polyethylene glycol polymers is present in the composition in an amount of from 80 weight % to 97 weight % by total weight of the composition.

The coating composition may be as defined herein. Preferably, the dental floss comprises the coating composition in an amount of from 30 weight % to 60 weight % by total weight of the floss (fibers) and coating composition. More preferably, the dental floss comprises the coating composition in an amount of from 45 weight % to 55 weight % by total weight of the floss (fibers) and coating composition. The final concentration of components provided in the coating composition mentioned herein (e.g. polyethylene glycol and peroxide source), once coated onto the dental floss, may be calculated accordingly. For example, a dental floss coated with a coating composition comprising polyethylene glycol in an amount of 80 weight % by total weight of the coating composition, wherein the amount of the coating composition is 50 weight % by total weight of the floss (fibers) and coating composition, will comprise polyethylene glycol in an amount of 40 weight % by total weight of the floss (fibers) and coating composition.

Thus in some embodiments, the dental floss may comprise polyethylene glycol in an amount of from 35 weight % to 48 weight %, from 35 weight % to 45 weight %, from 35 weight % to 42 weight %, or from 35 weight % to 40 weight %, by total weight of the floss (fibers) and coating composition. In some embodiments, the dental floss comprises polyethylene glycol in an amount of from 38 weight % to 48 weight %, from 38 weight % to 45 weight %, or from 38 weight % to 43 weight %, by total weight of the floss (fibers) and coating composition. Preferably, the dental floss comprises polyethylene glycol in an amount of from 40 weight % to 45 weight %, or from 40 weight % to 43 weight %, by total weight of the floss (fibers) and coating composition.

In some embodiments, the dental floss comprises a peroxide source in an amount of from 2 weight % to 10 weight % by total weight of the floss (fibers) and the coating composition. Preferably, the dental floss comprises a peroxide source in an amount of from 5 weight % to 10 weight %, or from 5 weight % to 8 weight %, or from 4 weight % to 10 weight %, or from 4 weight % to 6 weight %, by total weight of the floss (fibers) and the coating composition. In some embodiments, the dental floss comprises a peroxide source in an amount of from 5 weight % to 7 weight %, by total weight of the floss (fibers) and the coating composition.

Preferably, the peroxide source is present in the dental floss in an amount sufficient to deliver hydrogen peroxide in an amount of from 0.1 weight % to 3 weight %, or from 0.5 weight % to 3 weight %, or from 1 weight % to 3 weight %, by total weight of the floss (fibers) and the coating composition. In some embodiments, the peroxide source is present in the dental floss in an amount sufficient to deliver hydrogen peroxide in an amount of from 0.25 weight % to 2 weight %, or from 0.5 weight % to 2 weight %, or from 1 weight % to 2 weight %, by total weight of the floss (fibers) and the coating composition. In further embodiments, the peroxide source is present in the dental floss in an amount sufficient to deliver hydrogen peroxide in an amount of from 0.2 weight % to 1 weight %, or from 0.2 weight % to 0.5 weight %, by total weight of the floss (fibers) and the coating composition.

Methods of manufacturing dental floss are well known in the art. For example, dental floss may be produced from nylon. Typically, a nylon salt is polymerized and the resulting polymer is pumped or extruded to form monofilaments. The filaments are allowed to harden, and then combined to form a strand of floss. Dental floss may also be produced from polyretrafluoroethylene (PTFE or Teflon®), polypropylene polyethylene, styrene butadyene copolymers, and combinations thereof. The polymers are typically melted and extruded into thin strands.

Further provided herein is a method for coating dental floss comprising:
a) heating a coating composition to a temperature no greater than 50° C. to form a molten composition,
b) applying the molten composition to dental floss to coat the floss, and
c) cooling the composition so solidify the composition on the dental floss,
wherein the coating composition comprises one or more polyethylene glycol polymers and a peroxide source,
wherein the melting temperature of the one or more polyethylene glycol polymers, in combination, is from 38° C. to 50° C.,
and wherein the one or more polyethylene glycol polymers is present in the composition in an amount of from 80 weight % to 97 weight % by total weight of the composition.

The coating composition may be as defined herein.

The coating composition is preferably heated to a temperature of from 38° C. to 50° C., reflecting the melting point of the one or more polyethylene glycol polymers, and the temperature of the molten composition is maintained at a temperature not exceeding 50° C. By maintaining the temperature below 50° C., the rate of decomposition of peroxide to oxygen and water is minimized. In one embodiment, the dental floss is immersed in an emulsion bath containing the molten coating composition to enable the coating composition to adhere to the floss. The floss may then be lifted from the bath to enable cooling and subsequent solidification of the composition that has been coated on the floss.

In some embodiments, the floss is coated multiple times. Thus, once coated as described above, the method of coating may be repeated. This serves to increase the amount of coating composition on the floss.

Further provided is a dental floss obtainable by the method defined herein.

The floss may be in the form of a single ribbon (e.g., a Teflon® polyethylene ribbon). Alternatively, it may be bundle of thin filaments, e.g., nylon filaments. The number of filaments will be from about 2 to about 300, e.g., from about 2 to about 200, depending on the denier of the filaments. The filaments are twisted with about 1 to 5 twists per inch to form the floss. The twisting provides integrity of the floss on the spool and during subsequent handling. However, when used the filaments will spread out and splay against tooth surfaces. The floss may also be formed of interlocking fibers. In any case, the final floss product is preferably of a thickness that allows it to fit between the teeth. Where multiple filaments are used, the coating composition may applied before or after twisting, preferably after twisting. Other additives including desensitizing agents, antimicrobial agents, tartar control agents, mouth feel agents, sweeteners, flavorants, colorants, and fluoride sources, if not provided within the coating composition, may instead be applied to the coated floss after coating. The additives can be applied either as a liquid or a solid. It is preferred to use a spray dried solid. When applied as a liquid, the floss is dried prior to being wound onto a spool. The drying can be by radiant drying or air drying.

In some embodiments, provided herein is a dental floss comprising a coating composition as defined herein, optionally obtainable by the methods defined herein, wherein the coating composition is provided on the floss in a discontinuous fashion. By "discontinuous", it is meant that at least one segment of the floss is not coated with the coating composition as defined herein, or at least one segment of the floss is coated with a masking composition that is different from the coating composition. By "discontinuous", it may also be meant that at least one segment of the floss comprises or is coated by the coating composition as defined herein, and is further coated (or covered) by a masking composition. These types of segment may be referred to as "uncoated segments". Typically, the masking composition is free of a peroxide source and/or is insoluble on contact with a user. The segments of the floss comprising or coated by the coating composition as defined herein (without any further coating or covering by a masking composition) may be referred to as "coated segments".

Typically, the floss comprises a plurality of uncoated segments. Preferably, the coated and uncoated segments are arranged in an alternate fashion. The length of the uncoated segments is typically from 20 to 100 mm, and preferably from 30 mm to 40 mm. The length of the coated segments is preferably from 50 mm to 200 mm, and more preferably from 100 mm to 150 mm. By providing a discontinuous coating as described herein, the consumer is able to hold the uncoated segments of the floss without contacting the coated segments. Since the uncoated segments are either free of any coating composition, or comprise an outer covering of a masking composition which is either free of a peroxide source and/or is insoluble in water, adverse or irritating effects on the skin that may be caused by the peroxide source are avoided.

It is desirable that the consumer is able to distinguish the uncoated segments from the coated segments. In one embodiment, the coated segments have a different color to that of the uncoated segments. For example, in one arrangement, the coated segments are not colored, and the uncoated segments are colored. The coating composition or masking composition may comprise any of the following colorants to distinguish the coated segments from the uncoated segments: FD&C Blue #1, FD&C Yellow 13:1, FD&C Yellow #5, FD&C Red 40, FD&C Red #33, FD&C Green #3, FD&C Yellow #6 and D&C Violet #2. In another embodiment, the coated segments may be distinguished from the uncoated segments through differing diameters of the floss regions and/or through different textures.

A discontinuous coating may be achieved by applying a molten coating composition as defined herein in a discontinuous fashion during the floss manufacturing process, prior to cooling to solidify the coating composition on the floss. Alternatively, the floss may be coated continuously with a molten coating composition by the methods defined herein. Subsequently, a molten masking composition may be applied to the coated floss in a discontinuous fashion, prior to cooling to solidify the masking composition on the floss.

Dental floss is commonly supplied in plastic dispensers that contain 10 to 50 meters of floss. The dispenser typically has a small protected blade used to sever the floss when a desired amount is pulled out.

As mentioned above, the present inventors have found that polyethylene glycol polymers may serve as suitable replacements for wax as dental floss coating materials. In particular, by using a dental floss coating composition comprising one or more polyethylene glycol polymers which, in combination, have a melting point below 50° C., it is not necessary to use high heating temperatures to melt the composition during the floss manufacturing process. As such, additives such as peroxide may be incorporated into the coating composition without significant decomposition that would otherwise be observed at high heating temperatures.

Accordingly, in a further arrangement, provided herein is a use of one or more polyethylene glycol polymers, in a dental floss coating composition comprising a peroxide source, to prevent or reduce the rate of decomposition of the peroxide source in the composition, when the composition is in molten form. The coating composition may be as defined herein.

Still further provided is a method of preventing or reducing the rate of decomposition of a peroxide source in a dental floss coating composition, when the composition is in molten form, wherein the method comprises incorporating one or more polyethylene glycol polymers in the coating composition comprising the peroxide source. The coating composition may be as defined herein.

The rate of decomposition of peroxide is reduced relative to comparable compositions comprising animal, vegetable and synthetic waxes having a melting point above 50° C. in place of the one or more polyethylene glycol polymers.

The following Examples illustrate methods of the invention and their uses. The Examples are illustrative and do not limit the scope of the invention.

EXAMPLES

Example 1—Stability of PVP-Peroxide in Polyethylene Glycol (PEG)—1500

In the first development phase, PVP-hydrogen peroxide complex was dispersed in molten PEG 1500 at a temperature of 45-50° C., by stirring the mixture in a stainless steel beaker on a hot plate, using an IKA Eurostar mixer at 500 rpm with (IKA R-1342; 4-bladed propeller) for 20 minutes. Under these conditions, air incorporation into the mixture was minimized. PVP-peroxide was also added to the mixture. The components of the mixture were as follows: 92.5% PEG 1500, 2% PVP and 5% PVP-hydrogen peroxide complex. The addition of PVP to the mixture retards the degradation of PVP-peroxide. Additionally, PVP improves the rheology of the coating composition such that the coating composition is more stable with a reduced tendency to sediment. PVP-hydrogen peroxide complex has from 17% to 22% hydrogen peroxide, and the final hydrogen peroxide concentration in the mixture was found to be 1.1%. After one month of storage at 25±2° C./60±5% RH, the final hydrogen peroxide concentration was 1.0%. This indicates that there was negligible peroxide decomposition in the PEG mixture.

Example 2—Dental Floss Prototype

A prototype dental floss formulation was developed by mixing 13.0% of PVP-hydrogen peroxide complex, 3.0% of PVP, 3.0% Mint powder flavor, 0.5% of sucralose in 80.5% of PEG1500, melted at 45° C. The temperature was maintained in the range of 45-50° C. The process conditions were the same as described in Example 1. The concentration of hydrogen peroxide active in the mixture was calculated to be around 2.4%. (Multifilament dental flosses yarns typically absorb from 40 to 60% of coating, and thus the theoretical concentration of hydrogen peroxide in the final product (dental floss) would be around 1%.) After mixing, the hydrogen peroxide content of the coating mixture was determined to be 2.4% indicating that there was no decomposition of hydrogen peroxide in the molten mixture. The mixture was subsequently stored at room temperature. After 30 days of storage at 25±2° C./60±5% RH, the peroxide concentration was determined to be 2.3%, indicating negligible hydrogen peroxide decomposition in the PEG mixture.

If other waxes such as mineral or vegetable waxes are subjected to heating in order to melt the waxes, the PVP-hydrogen peroxide complex is immediately degraded to water and oxygen at the high temperatures required for melting. Accordingly, it is impossible to apply the peroxide source on a dental floss or tape using such waxes.

The molten dental floss coating formulation of the present invention described above was successfully applied in pilot scale on Polypropylene yarn (790 decitex, 256 filaments, 256 torsions) in an amount of 48 weight using a standard manufacturing process.

Whilst particular embodiments of the invention have been illustrated and described, it will be obvious to those skilled in the art that various changes and modifications may be made without departing from the scope of the invention as defined in the appended claims.

What is claimed is:

1. A dental floss coating composition comprising:
   one or more polyethylene glycol polymers;
   a peroxide source, and
   one or more ingredients selected from a desensitizing agent, an antimicrobial agent, a tartar control agent, a mouth feel agent, a sweetener, a flavorant, a colorant, a fluoride source and a combination of two or more thereof;
   wherein the melting temperature of the one or more polyethylene glycol polymers, in combination, is from 38° C. to 50° C.,
   wherein the one or more polyethylene glycol polymers is present in the composition in an amount of from 80 weight % to 97 weight % by total weight of the composition; and wherein the composition has a viscosity of from 1 cm2/second to 3 cm2/second, as measured at 25° C. with a Brookfield Model LVTDV-11 with Spindle 1.

2. The composition of claim 1, wherein at least one of the one or more polyethylene glycol polymers has an average molecular weight of from 950 to 9000 Daltons.

3. The composition of claim 1, wherein the peroxide source comprises a peroxide compound selected from: hydrogen peroxide, peroxides of alkali and alkaline earth metals, organic peroxy compounds, peroxy acids, and mixtures thereof.

4. The composition of claim 3, wherein the peroxide source comprises hydrogen peroxide.

5. The composition of claim 3, wherein the peroxide source comprises a peroxide compound and a cross-linked polymer.

6. The composition of claim 5, wherein the peroxide source comprises crosslinked polyvinylpyrrolidone (PVP)-hydrogen peroxide.

7. The composition of claim 1, wherein the peroxide source is present in the composition in an amount of from 10 weight % to 20 weight %, by total weight of the composition.

8. The composition of claim 1, wherein the composition is substantially anhydrous.

9. The composition of claim 1, wherein the melting temperature of the one or more polyethylene glycol polymers, in combination, is from 42° C. to 48° C.

10. The composition of claim 9, wherein the melting temperature of the one or more polyethylene glycol polymers, in combination, is 45° C.

11. The composition of claim 1, further comprising polyvinylpyrrolidone.

12. The composition of claim 11, wherein the composition comprises polyvinylpyrrolidone in an amount of from 1 weight % to 4 weight % by total weight of the composition.

13. The composition of claim 1, comprising a solvent selected from ethanol, isopropyl alcohol, and cyclomethicone.

14. The composition of claim 13, wherein the solvent is present in the composition in an amount of from 5 weight % to 15 weight %, by total weight of the composition.

15. The composition of claim 1, in molten or liquid form.

16. A dental floss comprising the coating composition of claim 1.

17. The dental floss of claim 16, wherein the dental floss comprises at least one segment which is not coated with the coating composition.

18. The dental floss of claim 17, wherein the dental floss comprises a plurality of segments which are not coated with the coating composition.

19. The dental floss of claim 16, wherein the dental floss is comprised of one or more of polyamide, polyethylene, PTFE (polytetrafluoroethylene), polypropylene, and polyurethane.

20. A method of coating dental floss, wherein the method comprises:
   a) heating a coating composition according to claim 1 to a temperature no greater than 50° C. to form a molten composition,
   b) applying the molten composition to dental floss to coat the floss, and
   c) cooling the composition so solidify the composition on the dental floss.

21. The method of claim 20, wherein the composition is heated to a temperature of from 38° C. to 50° C.

22. A dental floss obtained by the method of claim 20.

* * * * *